United States Patent [19]

Mordwinkin

[11] 4,230,987
[45] Oct. 28, 1980

[54] DIGITAL EDDY CURRENT APPARATUS FOR GENERATING METALLURGICAL SIGNATURES AND MONITORING METALLURGICAL CONTENTS OF AN ELECTRICALLY CONDUCTIVE MATERIAL

[75] Inventor: George Mordwinkin, Scottdale, Pa.
[73] Assignee: Sensor Corporation, Scottdale, Pa.
[21] Appl. No.: 15,061
[22] Filed: Feb. 26, 1979
[51] Int. Cl.$^3$ ............... G01N 27/72; G01R 33/12
[52] U.S. Cl. ............... 324/236; 324/228; 324/233
[58] Field of Search ............... 324/222, 226, 228, 233, 324/234, 236

[56] References Cited

U.S. PATENT DOCUMENTS

| | | | |
|---|---|---|---|
| 3,229,198 | 1/1966 | Libby | 324/233 |
| 3,314,006 | 4/1967 | Hentschel | 324/233 |
| 4,059,795 | 11/1977 | Mordwinkin | 324/233 |
| 4,086,527 | 4/1977 | Cadot | 324/233 |

*Primary Examiner*—Gerard R. Strecker
*Assistant Examiner*—Walter E. Snow
*Attorney, Agent, or Firm*—Buell, Blenko & Ziesenheim

[57] ABSTRACT

The apparatus comprises a parallel coil and a capacitance, the coil having an air gap in which an unknown specimen is inserted, a source of alternating voltage applied to the coil-capacitance combination, scanning means for automatically varying the value of the capacitance in steps, thus varying the phase of the voltage across the coil, means for digitizing the phase of the voltage corresponding to each capacitance value, a memory in which those digitized phase values are stored, a reference memory containing digitized phase values for known specimens, and means for comparing the digitized phase values of the unknown specimen with those of known specimens. A digital tolerance control circuit is also provided which accommodates deviations between the reference and the known phase values, up to predetermined amounts, and means are provided for displaying the generic name or grade of the stored phase values which match the phase values of the unknown specimen.

9 Claims, 4 Drawing Figures

BLOCK DIAGRAM

BLOCK DIAGRAM

TIMING DIAGRAM

DIGITAL EDDY CURRENT APPARATUS FOR GENERATING METALLURGICAL SIGNATURES AND MONITORING METALLURGICAL CONTENTS OF AN ELECTRICALLY CONDUCTIVE MATERIAL

RELATED PATENT

This invention is an improvement on the apparatus of my U.S. Pat. No. 4,059,795 of Nov. 22, 1977, DIGITAL EDDY CURRENT APPARATUS FOR SENSING AND ANALYZING METALLURGICAL CHARACTERISTICS OF AN ELECTRICALLY CONDUCTIVE MATERIAL.

This invention relates to eddy current apparatus for non-destructive identification of metals. It is more particularly concerned with such apparatus which identifies metal specimens in digital terms and automatically compares the digitized identification with predetermined digitized identifications of various metals and alloys stored in its memory so as to produce an output in terms of the grade or generic name of the specimen material.

THE PROBLEM AND THE PRIOR ART

Eddy current testing equipment is well known and is mentioned in my patent above identified. Prior to the invention of that patent, eddy current testing apparatus identified metals in accordance with their eddy current characteristics related to composition, hardness, heat treatment and the like, but did not present the information in a form which could be digitized and digitally displayed or used in a computer for rapid analysis. The apparatus of my patent presents the desired information in digital form. It is not, however, fully automated because the optimum operating point in terms of the frequency of the probe current must be determined experimentally by the operator.

STATEMENT OF THE INVENTION

As is well known, the presence of a metallic object or other electrically conductive material in the alternating magnetic field of an inductive sensing element will cause changes in its impedance because of eddy currents generated in the object.

I provide a resonating circuit comprising a coil and capacitance connected in parallel. When a specimen to be identified is brought in proximity to the coil in a predetermined air gap, the eddy currents induced in the specimen bring about a change in the impedance of the coil and so change the resonant condition of the coil-capacitance combination. The output voltage, therefore, is thus altered both in amplitude and phase.

I also provide means for automatically changing in discrete steps the value of the resonating capacitance. Thus, the specimen is scanned, or its output phase measured for each resonant condition corresponding to a capacitance step. The non-linear change of phase of the signal voltage, which may be called a metallurgical signature of the specimen, is then stored in a computer-type memory, which is also a part of my apparatus.

My apparatus includes a reference memory in which are stored the metallurgical signatures of commercial grades of various metals and alloys, and my apparatus includes means for comparing the metallurgical signature of the specimen with signatures stored in the reference memory. The sensitivity of my apparatus is high enough that it could present difficulties where metal grades with wide tolerances are concerned, or where there may be overlap between grades. To overcome that difficulty, I provide a digital tolerance control circuit which accommodates deviations between signatures, typically up to plus or minus nine counts. I also include means for displaying the stored signature which best matches the signature of the specimen, in terms of its commercial grade number of generic name.

My apparatus comprises a waveform generator which provides a set of logic waveforms required for phase digitizing, for driving the inductive sensing element, for automatic resonance scanning of the sensing element and for automatic tolerance adjustment. All those waveforms are functions of the frequency input to the waveform generator so that change in that input frequency brings about automatic adjustment of all timing waveforms. In this way multiple frequency scanning operation is readily carried out.

Thermal drift in the inductive sensing element is circumvented in my apparatus by a constant-current driver for that element which maintains a constant current through the element regardless of change of resistance of the sensing element winding. That constant current maintains the inductance of the winding at a constant value. Phase readings of the sensing element output will therefore remain accurate regardless of the change in the ambient temperature. The amplitude of the output signal will vary in proportion to resonance change, and to the change in the resistive component of the sensing coil impedance, but in my apparatus, I measure phase change only.

My apparatus includes a bias generator for the input stage of the signal amplifier that tracks the threshold level of the amplifier integrated circuit and compensates the input stage for thermal variations. This refinement makes possible extremely stable amplifier operation.

DESCRIPTION OF DRAWINGS

An embodiment of my invention presently preferred by me is illustrated in the attached drawings, to which reference is now made.

DETAILED DESCRIPTION

SENSING MEANS, DRIVING MEANS, AMPLIFIER AND BIAS GENERATOR

The sensing means comprise an inductive sensing head 15 parallel by a capacitance selected from capacitor bank 16.

Figure 3:
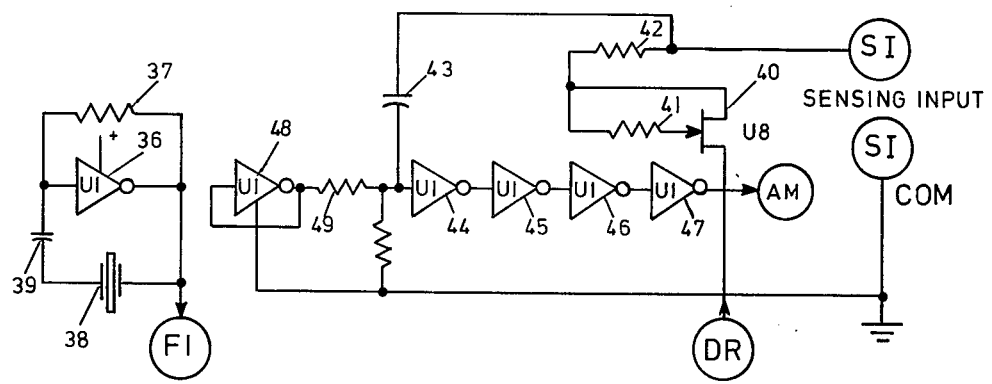
FIG. 3 is a schematic diagram of my crystal oscillator, constant current driver, and bias generator.

FIG. 3 is a schematic diagram of the crystal oscillator 11, constant current driver 17, amplifier 18 and bias generator 19. These are all comprised in six-element buffer inverter integrated circuit U1 and JFET U8, together with auxiliary components to be mentioned.

Oscillator 11 comprises one element 36 of U1 paralleled by feedback resistor 37, and crystal 38 in series with capacitor 39.

Constant-current driver 17 comprises transistor 40, which is element U8, connected in series with driver input voltage DR and ungrounded sensing input terminal SI. A limiting resistor 42 is interposed between terminal SI and the drain of transistor 40 to provide isolation between those elements and to prevent reactive shift influence on the constant-current supply and distortion of the square waveform of voltage DR.

Amplifier 18 comprises four elements 44-47 inclusive of buffer inverter U1 connected in cascade, the input of first stage 44 being coupled to ungrounded terminal SI by capacitor 43.

Bias generator 19 comprises element 48 of U1 having its input connected to its output and to the input of element 44 through resistor 49.

OPERATION OF SENSING MEANS

The operation of my sensing means is the same as that of the sensing means in my U.S. Pat. No. 4,059,795.

OPERATION OF DRIVING MEANS

The crystal controlled oscillator 11 of my driving means has a frequency in the range 1 MHz-10 MHz. The oscillator generates a square wave, F1 in FIG. 2. A square wave, of course, is one having a very rapid rise and fall and a flat top so that its corners are right angles. The square wave F1 is supplied to a conventional frequency divider 12 which produces a range of frequencies F2 from MHz to KHz as may be required. The selected output F2 from frequency divider 12 is introduced into waveform generator 13. As will be described, that generator generates a number of frequencies, including a sensing or driving frequency, DR which is a square wave.

Sensing driving pulses DR which, as has been mentioned, have a frequency which is a derivative of frequency F2, are applied to the inductive sensing head 15 through constant current driver 17. The advantages of a constant current driver have been mentioned above.

OPERATION OF AMPLIFIER

The amplifier 18 is operated in the class C (saturated) mode so as to produce rectangular output pulses AM. The width of a pulse AM is proportional to the amplitude of the signal. The bias generator 19 is adjusted so that an output of amplifier 18 is secured at the lowest signal amplitude, which occurs at the extreme point of phase change. The signal pulse AM is located with reference to the driving waveform DR in direct proportion to the phase relation between those two signals, the signal pulse AM for resonance condition being positioned in the center of the half of the rectangular wave DR.

OPERATION OF BIAS GENERATOR

The basic cause of thermal drift in semiconductors is change in threshold voltage level at the semiconductor junction. That change directly affects the stability of the stage when it is used for amplification of small analog signals. The integrated circuit U1 used in amplifier 18 and bias generator 19 is uniquely adapted to thermal drift stabilization because all six elements are made from the same material and are closely spaced so as to display the same thermal drift characteristics. Bias generator 19, having input of element 48 connected to its output, generates a DC voltage equal to the threshold voltage of the semiconductor junction of element 48 and all other elements of U1, as they are on the same silicon chip. That voltage instantaneously reflects any change in threshold voltage of all other elements on the same chhip connected thereto and provides perfect drift compensation.

RESONANCE SCAN CONTROl AND ADDRESS GENERATOR

Resonance scan control 20 switches capacitors of capacitor bank 16 across inductive sensing head 15. It comprises buffer-drivers U11 and JFET analog gates U12 and U13.

Figure 1:
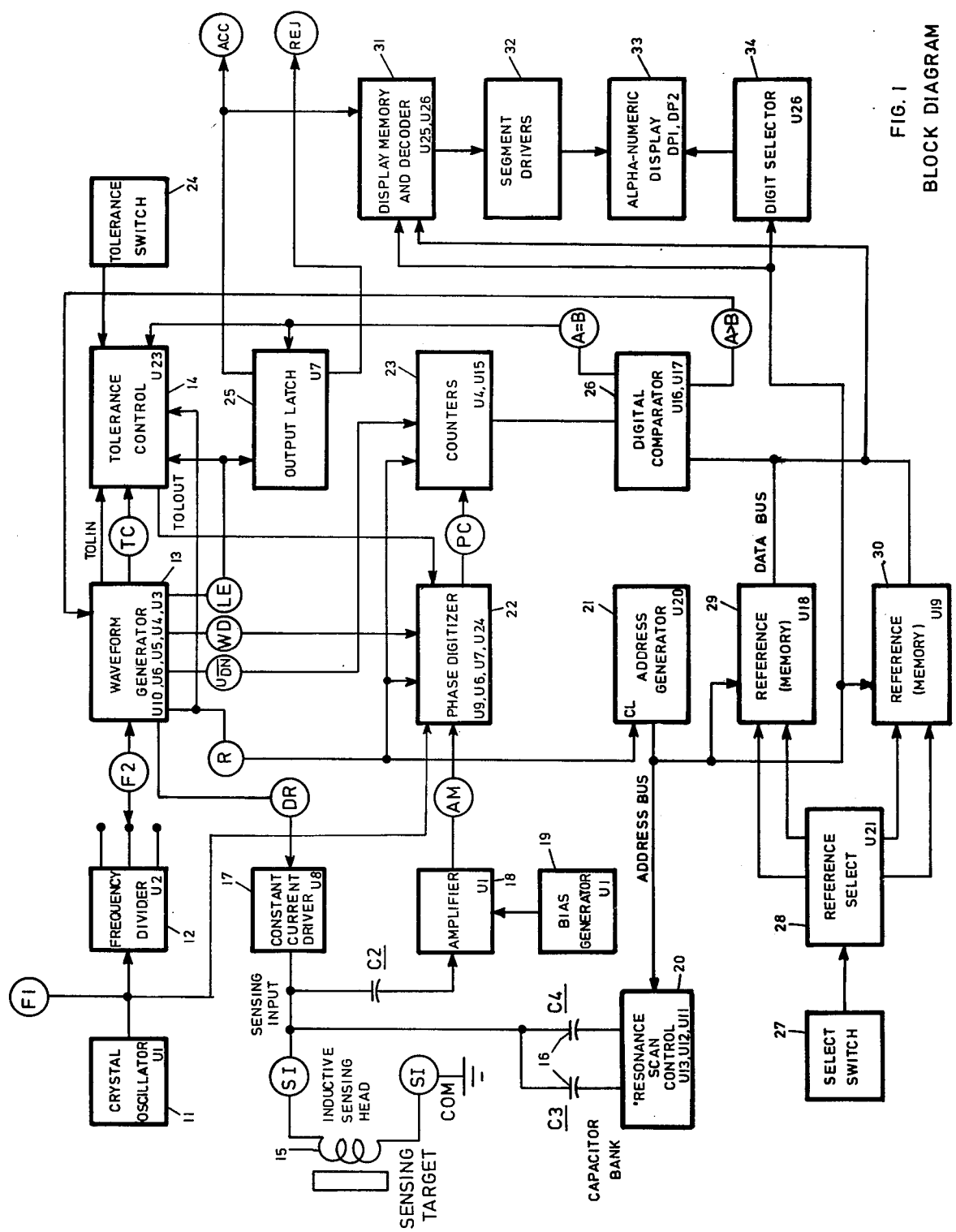
FIG. 1 is a block diagram of the apparatus of my invention.

The capacitor bank comprises 8 capacitors which are incorporated for convenience in two units, as is shown in FIG. 1. The capacitors have values of 100, 200, 400, 800, 1600, 3200, 6400 and 12,800 mmf respectively, but other values may be used.

Figure 4:
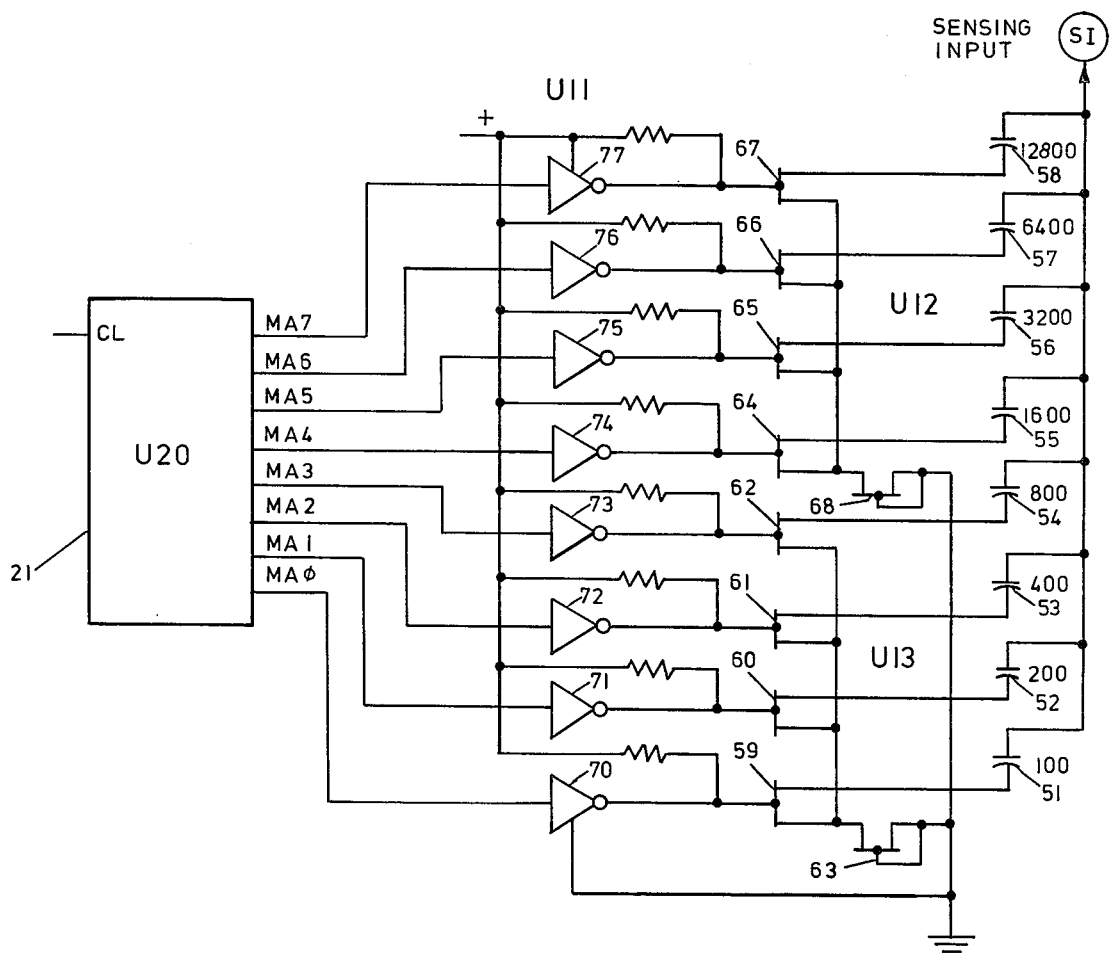
FIG. 4 is a schematic diagram of my resonance, scan control means.

FIG. 4 is a schematic diagram of the resonance scan control circuit 20 and its address generator 21. Eight capacitors 51-58 inclusive each have one terminal connected to a lead to ungrounded sensing terminal SI. The remaining terminals of each capacitor 55-58 inclusive are connected respectively to the drains of JFET transistors 64-67 inclusive, and the remaining terminals of capacitors 51-54 inclusive are connected respectively to the drains of JFET transistors 59-62, inclusive. The sources of transistors 64-67 are connected together and through compensating transistor 68 to ground. The sources of transistors 59-62 inclusive are connected together and through compensating transistor 63 to ground. The junctions of transistors 59-62 and 64-67 are connected to the outputs of buffer drives 70-77, respectively. The inputs of those buffer drivers are connected to the outputs of eight-bit address generator 21 and also to reference memories 29 and 30, to be described hereinafter.

Address generator 21 comprises dual binary up-counter U20. Reset signal R from waveform generator 13 is connected to the clock input of the up-counter. Eight Q lines are used as addresses to select eight lower order addresses of memories 29 and 30, used to store the reference signatures. The same eight lines are used to switch sequentially analog gates U12 and U13 of resonance scan control 20 through buffer drivers 70-77 inclusive.

OPERATION OF RESONANCE SCAN CONTROL AND ADDRESS GENERATOR

The JFET transistors in analog gates U12 and U13 are bipolar and require no DC potential on their drains. The AC voltage across sensing inductance 15 is applied to the drains of transistors 59-62 and 64-67 through the capacitors in capacity bank C3 and C4, as appears from FIG. 4.

A pulse from address generator 21 transmitted to buffer drive 77, for example, is passed on to the junction terminal of transistor 67, rendering it conductive so that the terminal of capacitance 58 connected to the drain of transistor 67 is connected to ground. That capacitor is thus shunted across terminals SI-SI$_{com}$. Other pulses from address generator 21 cause other capacitor elements to be connected to ground in the same way, so that an aggregate of 256 values of capacitance are switched in sequence across terminals SI-SI$_{com}$.

When a given specimen is positioned in inductive sensing head 15 there is, of course, only one value of capacitance from capacitor bank 16 which resonates the inductive sensing head at the frequency of sensing driver voltage DR. The voltage applied to amplifier 18 will have its maximum amplitude at that frequency, and will be approximately sinusoidal. All other values of capacitance will produce voltage inputs to amplifier 18 which are of lower amplitude and are out of phase with drive voltage DR, lagging or leading. Thus if all 256 values of capacitance 16 are switched in sequence, my apparatus will provide 256 different outputs from amplifier 18, each differing from all others in amplitude and/or phase, constituting the metallurgical signature of the specimen. Apparatus to be described hereinafter digitizes this phase change only, and compares it with reference signatures stored in a memory to identify metal specimens of unknown composition.

WAVEFORM GENERATOR

Waveform generator 13 comprises conventional integrated circuits conventionally connected to generate a set of logic waveforms all of which are submultiples of its input frequency F2, so that a change of input frequency automatically adjusts all timing frequencies.

Waveform generator 13 comprises decoder counter divider U3, dual flip-flops U4, U5 and U6, and hex "and" gate U10.

OPERATION OF WAVEFORM GENERATOR

The driving frequency DR is a fixed submultiple of frequency F2. I prefer to make it one-fortieth of F2. It is generated through decoder counter divider U3 and D type dual flip-flop U5. Tolerance control frequency TC is preferably fixed at one-tenth of frequency F2 and is generated by the same elements as is frequency DR, utilizing the other half of the dual flip-flop. Control pulses LE, update, and R, reset, are generated by "and" gating through one element of hex gate U10 frequency F2:2, which is one-half frequency F2, and an output from terminal 9 of decoder counter divider U3. Frequency F2:2 is generated by decoder counter divider U3 and half of flip-flop U4. Sensing window frequency WD is likewise generated through element U3 and half of flip-flop U6.

The decode counter divider U3 has 16 terminals, a number of which produce binary related timed outputs. Driving waveform DR is generated by the leading edge of pulses from terminals 3 and 1 which are used to set and reset one of the flip-flops U5. Tolerance control waveform TC is generated by the leading edge of pulses from terminals 5 and 9 applied to the other flip-flop of U5. Control pulses LE and R are generated by gating F2:2, generated by the pulses from terminal 13 and one flip-flop of U4, with the pulses from terminal 9 of U3. Sensing window waveform WD is generated by the leading edges of the pulses from terminal 11 of U3 which set one flip-flop of element U6. The end of that waveform is generated by the pulses from terminal 5 of U3 which reset that flip-flop.

Figure 2:
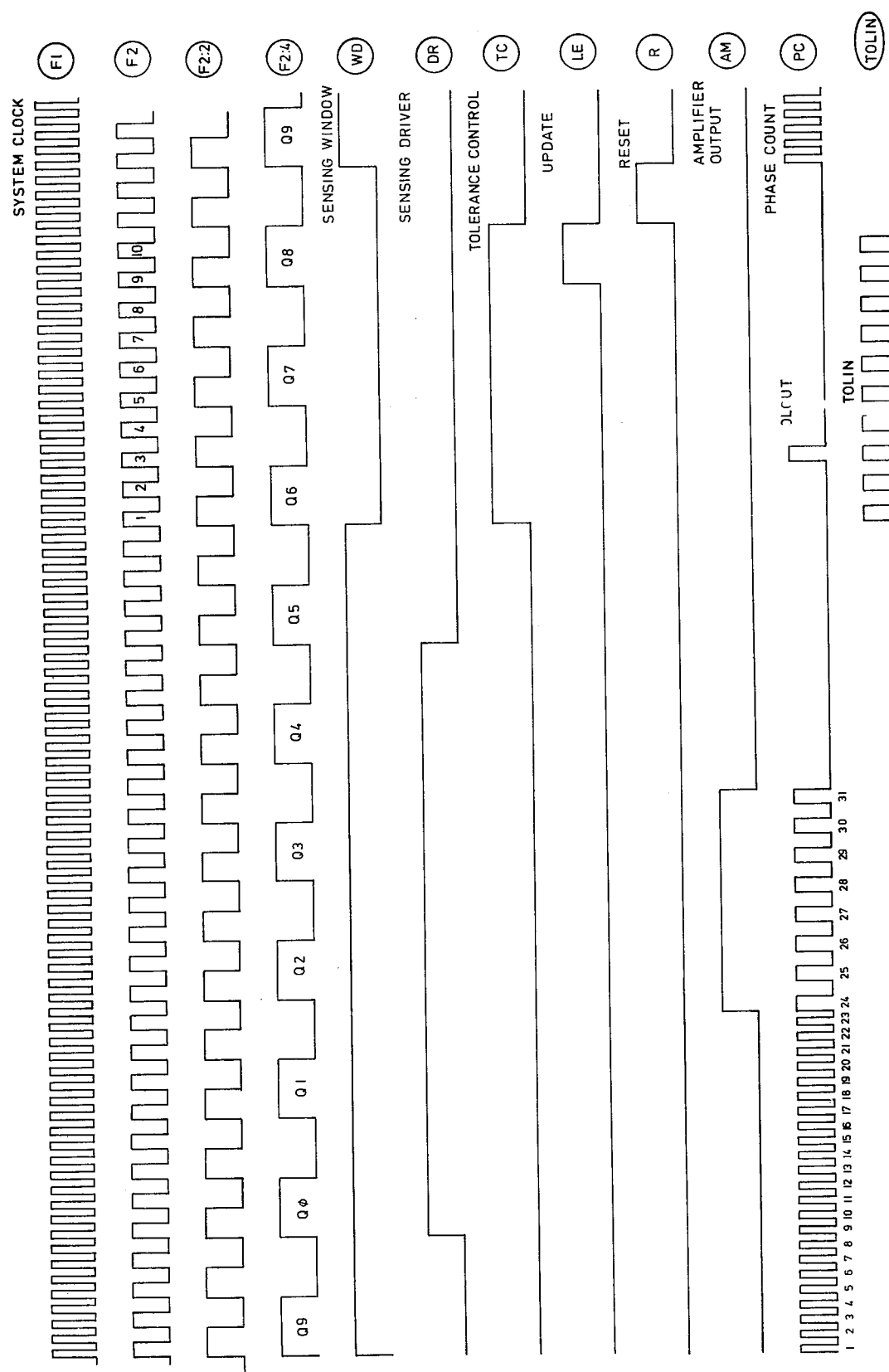
FIG. 2 is a timing diagram showing the waveforms developed by my waveform generator.

The waveform F2:4 in FIG. 2 is a waveform used internally in waveform generator 13. It has a frequency one-fourth that of frequency F2 and is generated therefrom through one-half of flip-flop U4. It is used as a clock for decoder counter U3 in the generation of waveforms WD, DR, TC, LE and R.

The elongated width of the sensing window waveform WD is to allow proper digitizing of the phase component of the sensing pulse AM, to be described hereinafter, even in extreme locations of plus or minus 90 degree phase, when the signal pulse width could extend beyond the edges of the waveform DR.

Sensing window WD sets the time limits where the phase relation between DR waveform and signal output waveform AM is digitized. Waveform TC defines the time when the tolerance control circuit 14 is operative. Waveform LE defines the time when display and logic circuits 31–34 inclusive are updated. Waveform R is the system reset signal, resetting all elements connected thereto before the start of each sensing cycle. Pulse U/DN described in more detail hereinafter controls the up/down counters 23.

The TOLIN waveform to tolerance control 14 is waveform F2 but is gated by tolerance control waveform TC so as to be transmitted only during tolerance control period TC, generating ten pulses at the input of rate multiplier U23.

PHASE DIGITIZERS AND COUNTERS

Phase digitizer 22 comprises CMOS analog gate U24, two D type flip-flops U6 and U7, and "and" gate U9. Counters 23 comprise BCD Up/Down counters U14 and U15.

OPERATION OF PHASE DIGITIZER AND COUNTERS

The purpose of the phase-digitizing circuit is to represent digitally the phase relation between driver reference waveform DR and the amplifier output pulse AM. That relation between two above mentioned signals is measured by counting the number of oscillator 11 pulses between the leading edge of the waveform WD and the center of the amplifier pulse AM.

The waveform WD is used instead of waveform DR so as to prevent a digitizing error when the pulse AM extends beyond the limits of waveform DR, especially when the phase angle of the signal is in the extreme position.

To achieve this goal the pulse train PC (phase count) is formed as follows:

At the leading edge of the waveform WD one of the analog gates of U24 is closed, feeding the F1 system clock pulses through terminal PC to counters U14 and U15.

As soon as the leading edge of pulse AM appears, the analog gate which feeds the F1 pulses opens, discontinuing further connection between F1 pulses and counters. At the same time another analog gate closes and feeds F1:2 pulses, which are at half rate of the F1 frequency, and which are generated by dividing F1 in one element of the flip-flops. When the trailing edge of AM appears, the second analog gate is also open.

No other pulses will reach line PC and counters 23 until the tolerance control period, during which a number of pulses (at the rate of frequency F2) may appear, if A=B condition of the digital comparator is not reached.

DIGITAL TOLERANCE CONTROL

The digital tolerance control circuit 14 consists of the rate multiplier U23 and tolerance switch 24.

OPERATION OF DIGITAL TOLERANCE CONTROL

In order to overcome the problem due to slight variations in the same alloys and grades of different heats, a special digital tolerance control circuit was developed. The purpose of this circuit is to provide a number of additional pulses through the phase count line PC to the counters, and achieve A=B condition between reference and test signatures.

Selector switch 24 selects the maximum allowed digital deviation between reference and the sample. A single switch will allow up to +nine pulses to achieve a match, and acceptance of the metal under test. An extended range of tolerance control can be achieved by using more than one switch and rate multiplier U23.

The principle of the operation of the tolerance control circuit is as follows:

Ten pulses at the rate of the frequency F2 are fed to the input terminal CL of U23 (TOLIN).

The number of outputs (TOLOUT) will be determined by the setting of switch 24.

As soon as terminal A=B of the digital comparator connected to the terminal STR of U23 becomes "true", the rate multiplier U23 is inhibited until the next sensing cycle.

Tolerance control circuit 14 is reset by the system reset pulse R.

REFERENCE, REFERENCE SELECT AND SELECT SWITCH

References 29 and 30 are CMOS EPROM memories U18 and U19 each having a storage capacity of 512×8 bits. In those reference memories 29 and 30 are stored the signatures of known metals and alloys for comparison purposes, as will be described. Select switch 27 provides manual selection of any signature from references 29 and 30 through reference select 28, which is a 4 bit latch/4-to-16 decoder. References 29 and 30 are also connected to be scanned by address generator 21.

OPERATION OF REFERENCE, REFERENCE SELECT AND SELECT SWITCH

Reference memories 29 and 30 are programmed by external memory programming means. Memories 29 and 30 store two signatures of 256 resonant points. They may also be programmed to store generic names of metallurgical signatures by reducing the number of resonance points stored, for example to 240, and utilizing the remaining 16 locations for generic names or codes numbers, such as "SAE 1010" and the like.

DIGITAL COMPARATOR AND OUTPUT LATCH

Digital comparator 26 comprises two digital comparator units U16 and U17. Their A inputs are connected to counters U14 and U15 of counter 23. Their B inputs are connected to one or the other of reference memories 29 and 30. The outputs of comparator 26 are A=B and A>B.

Output latch 25 is a D type flip-flop U7. The A=B signal of comparator 26 is applied to the "Data" input of output latch 25, and to tolerance control 14. The update LE signal is connected to the clock input. The A>B signal is applied to waveform generator 13.

OPERATION OF DIGITAL COMPARATOR AND OUTPUT LATCH

The A=B signal operates latch 25 to the accept position ACC and inhibits tolerance control 14. This occurs only when the signals from counter 23 and reference memory 29 or 30 match at the time the LE signal arrives.

The A>B signal triggers a pulse U/DN from waveform generator 13 which controls the up/down mode of the BCD up/down counters 23 during the tolerance control period TC. When the counter input to comparator 26 is larger than the reference input the A>B signal will switch counter 23 to the count-down method until A=B condition is reached, or until the end of the TC period is reached. In the latter event latch 25 will latch in the reject position REJ. The accept or reject signals ACC and REJ may be applied to any convenient visual display, audible signal means or machine control function.

Digital Comparator 26 also has an A>B output which is unused. Counters 23 are normally in the up-count mode and when the A<B condition obtains those counters automatically count up until the A=B condition is reached, or until the end of the TC period is reached.

DISPLAY

The display apparatus is conventional and comprises display memory and decoder 31 comprising 32×8 random access memory U25 and 4 bit latch/4-to16 decoder U26, segment drivers 32, alpha-numeric display 33, comprising 14 segment alpha-numeric LED display DP1 and DP2, and digit selector 34, 4 bit latch/4-to-16 decoder U26.

The outputs of reference memories 29 and 30 are connected to the input of display memory and decoder 31, as are the outputs of resonance scan control 20 and the accept signal ACC. The outputs of resonance scan control 20 are also connected to digit selector 34.

OPERATION OF DISPLAY

When address position 240 is reached and all 240 positions show a match between the stored signature and the signature of a specimen the address signal is advanced through positions 241-256 of the reference memory 29 or 30, and the contents of those locations are transferred to random access memory 31. As long as the A=B condition obtains at the output of digital comparator 26 during the time of up-date signal LE, that memory is continuously multiplexed through digit selector 34 and displays the transferred data which contains the generic name or code of the specimen.

The 16 digits, 241-256 inclusive accommodate all generic names or grades of signatures stored in memories 29 and 30. A list of standard and commercially available components used in the above described equipment as follows:

| Code | Designation | Function | Source |
|---|---|---|---|
| U1 | MC14049 | Buffer/Inverter | Motorola |
| U2 | MC14040 | Frequency Divider | Motorola |
| U3 | MC14017 | Decode Counter/Divider | Motorola |
| U4, U5, U6 and U7 | MC14013 | "D" type Flip/Flop | Motorola |
| U8 | 2N5457 | Transistor | Motorola |
| U9 | MC14081 | "AND" Gate | Motorola |
| U10 | MC14572 | Hex Gate | Motorola |
| U11 | DS8863 | Buffer/Drivers | National |
| U12, U13 | IH5009 | Analog Gate (2 FET) | Intersil |
| U14, U15 | CD4029 | BCG UP- Down Counter | RCA |
| U16, U17 | MC14585 | Digital Comparator | Motorola |
| U18, U19 | IM6604 | EPROM (512 × 8) | Intersil |
| U20 | MC14520 | Dual Binary Up Counter | Motorola |
| U21 | MC14515 | 4 Bit Latch/4-to-16 Decoder | Motorola |
| U23 | MC14527 | BCD Rate Multiplier | Motorola |
| U24 | MC14066 | CMOS Analog Gate | Motorola |
| U25 | CDP 1824 | 32 × 8 RAM | RCA |
| U26 | MC 14514 | BIT Latch/4-to-16 Decoder | Motorola |
| DP1, DP2 | MAN 2815 | 14 Segment Alpha-Numeric LED Display | Monsanto |
| DP3 | UDN 2982 | Segment Drivers | Sprague |

I claim:

1. Digital eddy current apparatus for identifying specimens of electrically conductive material of unknown composition comprising:
   (a) Driving means supplying a square wave which is used as reference;
   (b) Sensing means coupled to the driving means comprising an inductance, the impedance of which varies depending on eddy current characteristics of the specimen magnetically coupled thereto, and a capacitance connected with the inductance;
   (c) Scanning means for varying the value of said capacitance in steps over a range including the value which resonates with said inductance magnetically coupled to a specimen at the frequency of the driving means square wave and produces a voltage waveform thereacross which is in phase with the square wave, said range also including values of capacitance larger and smaller than the resonating value which produce voltage waveforms out of phase with the square wave;
   (d) Converting means coupled to the sensing means converting the voltage waveforms across the inductance corresponding to said values of capacitance connected therewith into rectangular pulse outputs, the rectangular pulse output corresponding to the resonating capacitance being positioned in the center of one-half the square wave, the rectangular pulses corresponding to other values of capacitance being offset from the center of one-half the square wave, said offsets being a function of the phase shift of the voltage waveforms; and
   (e) Means coupled with the converting means for monitoring the successive values of capacitance and the offsets of the waveforms corresponding to the respective capacitance values so as to provide a capacitance-offset relation which is a function of the metallurgical characteristics of the specimen.

2. Apparatus of claim 1 in which the driving means are coupled to the sensing means through a constant-current device whereby thermal drift of the sensing means inductance is minimized.

3. Apparatus of claim 2 in which the constant-current driving device comprises a transistor connected in series with the driving means and the sensing means.

4. Apparatus of claim 1 in which the converting means comprise a class-C operated signal amplifier.

5. Apparatus of claim 4 in which the signal amplifier is an integrated circuit, and including a bias generator connected to the input of the amplifier, said bias generator being physically a part of said integrated circuit and being adjusted to generate a direct current bias voltage equal to the threshold voltage of the input of the amplifier.

6. Apparatus of claim 5 in which the bias generator is an amplifier element having its input connected to its output and to the input of the signal amplifier.

7. Apparatus of claim 1 in which the monitoring means comprise means for digitizing the amounts of the offsets of the converting means output pulses, and including a memory connected with the scanning means holding capacitance-offset relations for specimens of electrically conductive material of known composition, and comparing means connected to the output of the digitizing means and the output of the memory so as to compare the successive digitized outputs of the offsets of the unknown specimen related to the successively scanned capacitance values with the correspondingly digitized offsets of known specimens in the memory.

8. Apparatus of claim 7 including tolerance control apparatus comprising means connected with the means for digitizing the amounts of the offsets for adding thereto, a fixed predetermined number of pulses.

9. Apparatus of claim 7 in which the memory holds in conjunction with capacitance-digitized offset relations for specimens of electrically conductive materials of known composition the common designation of those specimens, and including display means connected with that memory and with the scanning means for displaying the common designation corresponding to the capacitance-digitized offset relation of the unknown specimen.

* * * * *

UNITED STATES PATENT AND TRADEMARK OFFICE
CERTIFICATE OF CORRECTION

PATENT NO. : 4,230,987
DATED : October 28, 1980
INVENTOR(S) : GEORGE MORDWINKIN

It is certified that error appears in the above-identified patent and that said Letters Patent are hereby corrected as shown below:

Column 2, line 8, "of" should read --or--.

Column 4, line 4, "CONTROl" should read --CONTROL--.

Column 4, line 29, "buffer drives" should read --buffer drivers--.

Column 5, line 2, "drive voltage" should read --driver voltage--.

Column 8, line 5, "A > B" should read --A < B--.

Column 8, line 15, "4-to 16" should read --4-to-16--.

Column 8, line 64, the Function should read --4 BIT Latch/4-to-16 Decoder--.

Signed and Sealed this

Twenty-fourth Day of March 1981

[SEAL]

Attest:

RENE D. TEGTMEYER

Attesting Officer

Acting Commissioner of Patents and Trademarks